(12) United States Patent
Benameur et al.

(10) Patent No.: US 9,198,868 B2
(45) Date of Patent: Dec. 1, 2015

(54) BULK ENTERIC CAPSULE SHELLS

(75) Inventors: Hassan Benameur, Eaubonne (FR); Dominique Nicolas Cade, Colmar (FR); Sophie Schreiber, Colmar (FR)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 13/881,664

(22) PCT Filed: Oct. 24, 2011

(86) PCT No.: PCT/IB2011/002894
§ 371 (c)(1),
(2), (4) Date: Jul. 15, 2013

(87) PCT Pub. No.: WO2012/056321
PCT Pub. Date: May 3, 2012

(65) Prior Publication Data
US 2013/0287840 A1    Oct. 31, 2013

Related U.S. Application Data

(60) Provisional application No. 61/406,701, filed on Oct. 26, 2010.

(51) Int. Cl.
| A61K 9/48 | (2006.01) |
| B01J 13/04 | (2006.01) |
| C09B 67/02 | (2006.01) |
| A61K 31/167 | (2006.01) |
| A61K 47/38 | (2006.01) |

(52) U.S. Cl.
CPC ............. *A61K 9/4816* (2013.01); *A61K 31/167* (2013.01); *A61K 47/38* (2013.01); *B01J 13/04* (2013.01); *C09B 67/0097* (2013.01)

(58) Field of Classification Search
None
See application file for complete search history.

(56) References Cited

U.S. PATENT DOCUMENTS

| 2,718,667 | A |  | 9/1955 | Malm et al. |
| 3,493,407 | A |  | 2/1970 | Greminger, Jr. et al. |
| 3,617,588 | A |  | 11/1971 | Langman |
| 3,740,421 | A |  | 6/1973 | Schmolka |
| 4,001,211 | A | * | 1/1977 | Sarkar ............................ 536/84 |
| 4,138,013 | A |  | 2/1979 | Okajima |
| 5,264,223 | A |  | 11/1993 | Yamamoto et al. |
| 5,698,155 | A |  | 12/1997 | Grosswald et al. |
| 5,756,123 | A |  | 5/1998 | Yamamoto et al. |
| 2003/0161872 | A1 | * | 8/2003 | Chen et al. .................... 424/452 |
| 2007/0053869 | A1 |  | 3/2007 | Sugiyama et al. |
| 2007/0254033 | A1 |  | 11/2007 | Bhatt et al. |
| 2008/0248102 | A1 | * | 10/2008 | Rajewski et al. ............. 424/452 |
| 2009/0004263 | A1 |  | 1/2009 | Bhatt et al. |
| 2010/0158997 | A1 |  | 6/2010 | Dong |

FOREIGN PATENT DOCUMENTS

| CN | 1258500 A | 7/2000 |
| EP | 0223685 A2 | 5/1987 |
| EP | 0401832 A2 | 12/1990 |
| EP | 1447082 A1 | 8/2004 |
| GB | 1310697 | 3/1973 |
| JP | S57-142251 | 9/1982 |
| JP | 2006-505542 | 2/2006 |
| WO | WO 00/18377 | 4/2000 |
| WO | WO 2004/030658 A1 | 4/2004 |
| WO | WO 2007/027560 A2 | 3/2007 |
| WO | WO 2008/050209 A1 | 5/2008 |
| WO | WO 2008/119943 A2 | 10/2008 |
| WO | WO 2009/050646 A2 | 4/2009 |
| WO | WO 2009/138920 A1 | 11/2009 |

OTHER PUBLICATIONS

Felton et al., *Pharm Sci* 2002, 4, Abstract T3320.
Han et al., *Journal of Pharmaceutical Sciences*, vol. 98, No. 8, Aug. 2009.
Huyghebaert et al., *Eur J Pharm Sci* 2004, 21, 617-623.
International Search Report mailed Jun. 4, 2012 for International Application No. PCT/IB2011/002894.
Kirilmaz L., S.T.P. *Pharma Sciences*, Nov. 10, 1993 3/5, 374-378.
Thoma et al., *Capsugel Technical Bulletin* 1986, 1-16.
Felton, L.A. et al., "Enteric Film Coating of Soft Gelatin Capsules", Drug Development and Delivery, Sep. 2003, vol. 3, No. 6, posted on Mar. 28, 2008.
English-language translation of Search Report and Office Action issued in corresponding Chinese Patent Application No. 201180061971.1, Nov. 4, 2014 (13 pages).
English-language translation of Notice of Reasons for Rejection issued in corresponding Japanese Patent Application No. 2013-535531, Jul. 7, 2015 (8 pages).

* cited by examiner

*Primary Examiner* — Mina Haghighatian
*Assistant Examiner* — Luke Karpinski
(74) *Attorney, Agent, or Firm* — Klarquist Sparkman, LLP

(57) ABSTRACT

The present disclosure relates to aqueous compositions for use in the manufacture of capsule shells endowed with bulk enteric properties. The present disclosure also relates, in part, to aqueous dispersions suitable for the implementation of said manufacturing process, and to enteric capsule shells and hard capsules obtained therewith.

20 Claims, No Drawings

BULK ENTERIC CAPSULE SHELLS

This application is a national stage entry under 35 U.S.C. §371 of International Application No. PCT/IB2011/002894, filed Oct. 24, 2011 which claims priority of U.S. provisional application No. 61/406,701, filed Oct. 26, 2010, all of which are incorporated herein by reference in their entirety.

This application claims priority to U.S. Provisional Application No. 61/406,701, filed on Oct. 26, 2010, the disclosure of which is incorporated herein by reference in its entirety.

The present disclosure relates to aqueous compositions for use in the manufacture of capsule shells endowed with bulk enteric properties. The present disclosure also relates, in part, to aqueous dispersions suitable for the implementation of said manufacturing process, and to enteric capsule shells and hard capsules obtained therewith.

Capsules are well-known dosage forms that normally consist of a shell filled with one or more specific substances. The shell itself may be a soft or a hard stable shell. Hard capsule shells are generally manufactured using dip moulding processes, which can be distinguished into two alternative procedures. In the first procedure, capsules are prepared by dipping stainless-steel mould pins into a solution of polymer, optionally containing one or more gelling agents (e.g. carrageenans) and co-gelling agents (e.g. inorganic cations). The mould pins are subsequently removed, inverted, and dried to form a film on the surface. The dried capsule films are then removed from the moulds, cut to the desired length, and then the caps and bodies are assembled, printed, and packaged. See e.g., U.S. Pat. No. 5,264,223, U.S. Pat. No. 5,756,123, and U.S. Pat. No. 5,756,123.

In the second procedure, no gelling agents or co-gelling agents are used and film-forming polymer solution gelifications on the moulding pins are thermally induced by dipping pre-heated moulding pins into the polymer solution. This second process is commonly referred to as thermogellation or thermogelling dip moulding. See, e.g., EP 0401832, U.S. Pat. No. 3,493,407, U.S. Pat. No. 4,001,211, GB1310697, U.S. Pat. No. 3,617,588 and WO 2008/050209. In each of the aforementioned processes, both utilize a solution of the different ingredients that constitute the capsule shell wall.

Once the capsules are formed, different techniques have been used to impart enteric properties to the hard or soft capsule shells. One such technique involves treating the surface of the pre-manufactured capsules (e.g. spraying or film-coating already manufactured capsules) with one or more layers of a substance or composition that is known to impart enteric properties. However, this technique is time-consuming, complex, and consists of expensive multiple step process. In addition, hard capsule shells made by this process must typically be pre-filled and sealed, or banded, before the surface is treated. As a result, it is not possible to use this process to make or commercialize hard capsule shells in a pre-locked status. Thus, the determination of the adequate filling parameters is left with the end user.

In an attempt to overcome these drawbacks, another technique used to impart enteric properties to hard or soft capsule shells involves the direct use of enteric polymers (acid-insoluble polymers) within the context of the hard shell manufacturing process. Thus, in this technique, the impartation of the enteric properties occurs during the manufacturing process as opposed to treating capsules which have already been pre-formed. However, when enteric polymers are used in large amounts, which are otherwise theoretically necessary for commercialization of the hard capsule shells manufacture, enteric polymers are poorly or completely water insoluble. Thus, the use of the process on a commercial scale raises a significant problem with respect to the effectiveness at which one can use this process under conventional dip moulding techniques. In addition, this method of coating works well on a small scale for hydroxypropyl methylcellulose (HMPC) capsules, but in the case of gelatin capsules, poor adhesion of the coat to the smooth gelatin surface can result in brittleness of the capsule. See, e.g., Huyghebaert et al., *Eur J Pharm Sci* 2004, 21, 617-623; Felton et al., *Pharm Sci* 2002, 4, Abstract T3320, and Thoma et al., *Capsugel Technical Bulletin* 1986, 1-16.

Attempts to overcome the deficiencies discussed above range from (i) using low, water-soluble amounts of acid-insoluble polymers in combination with major amounts of conventional film forming polymers; (ii) salifying the water-insoluble polymers to obtain water-soluble derivatives; (iii) using solvent-based dipping solutions instead of water-based ones; and (iv) using alternative techniques, such as injection moulding, which do not require polymer solubilization. See e.g., WO 2004/030658; WO2008/119943; EP1447082; U.S. Pat. No. 4,138,013; U.S. Pat. No. 2,718,667; EP 223685A1; Han et al., *Journal of Pharmaceutical Sciences*, Vol. 98, No. 8, August 2009; and Kirilmaz L., S.T.P. *Pharma Sciences*, Nov. 10, 1993, 3/5 (374-378).

Despite this progress, many of the techniques described above still require the addition of enteric (acid insoluble polymer) polymers, require salts or pH regulators, require multiple processing steps, and/or need to be processed in non-aqueous media. Thus, there is a need to develop a rapid, safe, and economic way to generate hard capsule shells displaying enteric properties, while maintaining optimal chemical and mechanical properties, and without the need for conventional acid insoluble polymers and/or non-aqueous media, or requiring additional processing steps, e.g., coating the enteric polymer or double dipping.

Accordingly, one aspect of the present disclosure provides water-based compositions comprising cellulose acetate phthalate (CAP) that display appropriate solid content, viscosity at room temperature, setting properties, and rheological behavior for use in the manufacture of hard capsule shells.

In another aspect, the present disclosure relates to films and hard capsule shells obtained from the aforementioned water-based compositions, wherein the films and/or hard capsule shells display bulk enteric properties and exhibit optimal chemical and mechanical properties, e.g., disintegration profile, dissolution profile, film thickness, tensile strength values.

In another aspect, the present disclosure provides films and hard capsule shells displaying enteric properties, which are free of non-aqueous media/solvents.

In another aspect, the present disclosure provides rapid, economic, safe and easy to realize dip-moulding processes for the manufacture of hard capsule shells displaying bulk enteric properties (hereinafter also referred to as "enteric hard capsule shells"). In yet another aspect, the present disclosure provides a rapid, economic, safe and easy to realize "one step" dip-moulding process for the manufacture of hard capsule shells, wherein the co-presence of conventional film-forming non enteric polymers is no longer necessary.

DEFINITIONS

As used in the present disclosure, the following words, phrases, and symbols are generally intended to have the meanings as set forth below, except to the extent that the context in which they are used indicates otherwise.

As used herein, "optional" or "optionally" means that the subsequently described even or circumstance may or may not occur, and that the description includes instances where the event or circumstance occurs and instances in which it does not.

As used herein, "w/w %" means by weight as a percentage of the total weight.

The term "about" is intended to mean approximately, in the region of, roughly, or around. When the term "about" is used in conjunction with a numerical range, it modifies that range by extending the boundaries above and below the numerical values set forth. Unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Unless otherwise indicated, "cellulose acetate phthalate" is also referred to as CAP, and is commonly known in the field of polymers with the following alternative nomenclature: CAS registry number 9004-38-0; chemical common synonyms, such as: acetyl phthalyl cellulose, cellulose acetate hydrogen 1,2-benzenedicarboxylate, cellulose acetate hydrogen phthalate, cellulose acetate monophthalate, cellulose acetophthalate, and cellulose acetyl phthalate; and non proprietary names, such as: cellacephate (British Pharmacopeia), cellulose acetate phthalate (Japanese Pharmacopeia), cellulosi acetas phthalas (PhEur), and cellacefate (US Pharmacopeia).

Unless otherwise indicated, "non-salified CAP" means that CAP free acid residues (e.g., the carboxylic acid residues of the phthalate and acetate moieties present in the molecule) are not salified. For example, salification with carbonates, bicarbonates, hydrogen phosphates and hydroxides of elements of Groups I and II of the periodic table, or nitrogen containing base compounds (e.g., ammonia or primary, secondary or tertiary organic amines or amine derivatives), are excluded. The CAP may be non-salified in any one of the manufacturing steps of the hard capsule shells and capsules as described herein. Nonetheless, unwanted salification of technically irrelevant amounts of CAP may be tolerated as the result of the presence of salifying basic impurities in other ingredients used in the manufacturing processes for the hard capsule shells and capsules. Similarly, if purchased non-salified CAP contains salified CAP as an impurity, this is tolerable. In some instances, traces or impurities of salified CAP can be present in the aqueous compositions, hard capsule shells or capsules of the present disclosure. Traces or impurities of salified CAP can be, for example, less than 1% by weight over the weight of the total CAP present.

Unless otherwise indicated, the CAP is present in a dispersed state in the aqueous compositions described herein. Thus, the aqueous compositions comprise finely divided non-salified CAP solid particles having average diameters ranging from about 0.1 to about 10 microns. CAP dispersions are commercially available and can be either purchased (e.g. FMC Aquacoat® CPD30) or obtained by re-dispersing a commercially available powdered non-salified CAP (e.g. the FMC Aquateric® product or CAP available from Eastman chemical) in water. It will be understood that other ingredients in the aqueous compositions described herein, e.g., the processing aids, may be present in the dissolved state, dispersed state, or mixtures thereof depending on the solubility properties of the other ingredients.

The term "solids" includes at least all non-aqueous ingredients present in the aqueous compositions, capsule shells, and capsules described herein. For example, "solids" include, but are not limited to, ingredients a) (or A)) and b) (or B)), plus any additional and optional ingredients. For example, solids include CAP (for example CAP from Eastman), the processing aid, all optional non-aqueous ingredients pre-formulated in commercially available CAP products, e.g., FMC Aquateric or Aquacoat CPD 30®. Other solids are discussed below in connection with optional ingredients of the aqueous compositions, capsule shells, and capsules described herein.

Unless otherwise indicated, hard capsules described herein have the same or similar shape of commercially available, conventional hard capsules intended for oral administration to human or animal subjects. The hard capsules described herein can be manufactured using different processes, such as the dip moulding processes discussed below as well as the use of conventional equipment. As is described in detail below, pin moulds may be dipped into an aqueous-based film forming composition and subsequently withdrawn. The film formed on the moulding pins surface can then be dried, stripped off the pins and cut to a desired length, thereby obtaining the capsules caps and bodies. Normally, caps and bodies have a side wall, an open end and a closed end. The length of the side wall of each of said parts is generally greater than the capsule diameter. The capsule caps and bodies may be telescopically joined together so as to make their side walls partially overlap and obtain a hard capsule shell.

As described herein, the term "partially overlap" is intended to encompass the side walls of caps and bodies having the same or similar length such that when a cap and a body are telescopically joined, the side wall of said cap encases the entire side wall of said body.

Unless otherwise indicated, "capsule" refers to filled capsule shells whereas "shell" specifically refers to an empty capsule. Since the hard capsule shells described herein can be filled with substances in liquid form, the hard capsules may be sealed or banded according to conventional techniques. Alternatively, the hard capsule shells can be manufactured to have a specific capsule shell design that provides certain advantages over conventional techniques, e.g., the ability to pre-lock empty caps and bodies, or completing the filling steps in a different location, or at a specific time. Examples of such designs may be found it, for example, WO 2009/138920 and WO 2009/050646.

The term "active ingredient" is used to indicate a component of the compositions, capsule shells, and capsules described herein that is pharmaceutically or physiologically active. Thus, it would be understood that any compound that is pharmaceutically or physiologically active, or that may take the benefit of delayed release, is considered to be an active ingredient. For example, acetaminophen, ibuprofen, or caffeine would be considered active ingredients.

Unless otherwise indicated, "bulk enteric properties" means that the capsule shells described herein are soluble in, or disintegrated by alkaline intestinal secretions, but are substantially insoluble or resistant in acid secretions of the stomach. Disintegration and dissolution properties can be tested according to <701>, USP34-NF29, page 276; <711>, USP34-NF29, page 278; and <2040>, USP34-NF29, page 871.

In one embodiment, the present disclosure provides an aqueous composition for the manufacture of enteric hard capsule shells, said composition comprising:

(a) an aqueous dispersion of non-salified cellulose acetate phthalate (CAP), said CAP being present in an amount ranging from about 10% to about 40% by weight of the total weight of said aqueous composition;

(b) at least one processing aid present in an amount ranging from about 4% to about 20% by weight of the total weight of said aqueous composition, wherein said at least one processing aid is selected from polyoxyethylene-polyoxypropylene-polyoxyethylene tri-block polymers or mixtures thereof, and comprise an average molecular weight ranging from about 1000. to about 20000 and a polyoxyethylene ratio ranging from about 10% to about 85%; and (c) water.

In one embodiment, CAP is the only polymer displaying enteric properties in the aqueous compositions. Thus, in one embodiment the aqueous compositions do not contain polymers, except CAP, which display enteric properties, e.g., polymers such as polymethacrylates (copolymer of methacrylic acid and either methyl methacrylate or ethyl acrylate—e.g. Eudragit® enteric family members such as Eudragit® L); non CAP cellulose based polymers e.g. CAT (cellulose acetate trimellitate); HPMCAS (hypromellose acetate succinate); HPMCP (hydroxypropyl methylcellulose phthalate); CMEC (Carboxy Methyl Ethyl Cellulose); or polyvinyl derivatives e.g. polyvinyl acetate phthalate (Coateric® family members).

An advantage of the aqueous compositions herein is that the CAP amounts described allow for the manufacture of the hard capsule shells, e.g. using a dip-moulding process, without the need to incorporate other film-forming polymer(s) that are conventionally used as base film-forming polymers for hard capsule shells. In other words, non-salified CAP can be used along with the processing aids in amounts that provide films endowed with sufficient film forming properties such as thermal properties (DSC and MFT), thermo-rheological properties and mechanical properties (e.g. Young's module and brittleness). Accordingly, in one embodiment, the aqueous compositions may comprise film-forming polymer(s) conventionally used as base film-forming polymers for hard capsule shells in amounts less than 5% by weight, e.g., less than 1% by weight over the weight of the shell. Alternatively, in one embodiment, the aqueous compositions do not contain film-forming polymer(s) conventionally used as base film-forming polymers for hard capsule shells.

In one embodiment, film-forming polymer(s) conventionally used as base film-forming polymers for hard capsule shells include, for example, cellulose non enteric derivatives. Examples include HPMC (e.g. HPMC types 2910, 2906 and/or 2208 as defined in USP30-NF25), gelatin, pullulan, PVA and non enteric starch derivatives, such as hydroxypropyl starch.

In one embodiment, the processing aid comprises a polyoxyethylene-polyoxypropylene-polyoxyethylene block polymer—ingredient b) and B). This ingredient is also known in the field of polymers with the following synonyms: polyoxyethylene-propylene glycol copolymer, polyoxyethylene-polyoxypropylene copolymer; commercial names of families of polyoxyethylene-polyoxypropylene-polyoxyethylene block polymers are: Lutrol®, Monolan®, Pluronic®, Supronic®, Synperonic®; CAS name α-Hydro-ω-hydroxy-poly(oxyethylene)poly(oxypropylene)poly(oxyethylene) block copolymer; CAS number 9003-11-6. Reference below is made to ingredient b), only. However, these references must be understood as being valid also for ingredient B), since both ingredients comprise a polyoxyethylene-polyoxypropylene-polyoxyethylene block polymer.

In one embodiment ingredient b) is selected from poloxamers and mixtures thereof. Poloxamers are well-known non-ionic polymers. Examples of poloxamers may be found in, e.g., U.S. Pat. No. 3,740,421.

The language poloxamer or poloxamers refers to polyoxyethylene-polyoxypropylene-polyoxyethylene (POE-POP-POE) triblock copolymers having the following Formula (I):

Formula (I)

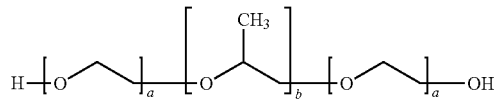

wherein a and b are integers and determined by the initial amounts of POE and POP used in the polymerization process as well as the polymerization process conditions. Within the molecular weight range of between about 1000 to about 20000, appropriate a/b ratios can be selected based on the desired hydrophilic/hydrophobic properties of the final polymer (since the POE blocks bring hydrophilicity whereas POP blocks bring hydrophobicity).

In one embodiment, poloxamers suitable in the context of the present disclosure, include those for which the hydrophile-lipophile balance (HLB) of the hydrophilic and lipophilic moieties is higher than 5, such as higher than 7, and higher than 12.

In one embodiment, poloxamers are selected from those defined in the USP32-NF27 "poloxamers" monograph. Examples of such products are Poloxamer 124 and Poloxamer 188, having an average MW range of 2090 to 2360 and 7680 to 9510 respectively; and a polyethylene oxide ratio of about 45% to about 80% respectively. Mixtures of poloxamers, such as USP32-NF27 poloxamers, are also within the scope of the invention.

In one embodiment, the polyoxyethylene-polyoxypropylene-polyoxyethylene block polymer comprises Poloxamer 124 (commercially available from BASF as Lutrol® L44).

In one embodiment, the polyoxyethylene-polyoxypropylene-polyoxyethylene block polymer comprises or consists of Poloxamer 188 (commercially available from BASF as Pluronic® F68NF).

In one embodiment, the polyoxyethylene-polyoxypropylene-polyoxyethylene block polymer comprises a mixture of poloxamers 124 and 188.

In one embodiment, the polyoxyethylene-polyoxypropylene-polyoxyethylene block polymer is a mixture comprising, Poloxamer 188 and Poloxamer 124 as defined wherein the ratio between the amounts of Poloxamer 124 and Poloxamer 188 ranges from 0 to about 0.9, such as from about 0.2 to 0.9, and from about 0.7 to about 0.9.

In one embodiment, the processing aid comprises, a polyoxyethylene-polyoxypropylene-polyoxyethylene tri-block polymer having an average molecular weight ranging from about 1000 to about 20000, said processing aid being present in an amount ranging from about 4% to about 20% by weight over the total weight of aqueous composition of the invention.

In one embodiment, the processing aid comprises, a mixture of polyoxyethylene-polyoxypropylene-polyoxyethylene tri-block polymers, each polymer in the mixture having an average molecular weight between about 1000 to about 20000, said processing aid being present in an amount between about 4% to about 20% by weight over the total weight of aqueous composition.

In the aqueous compositions described herein, as well as the shells described herein, a processing aid as defined above is present in an amount ranging from about 4% to about 20% by weight, such as from about 4% to about 15% by weight, and from about 5% to about 11% by weight over the total weight of aqueous compositions.

In one embodiment, the aqueous composition comprises a total amount of solids, such as CAP and the at least one processing aid, ranging from about 14.9% to about 50% combined, by weight of the total weight of the composition. In other embodiments, the total amounts of solids range from about 20% to about 50% and about 25% to about 40% by weight of the total weight of the composition.

In one embodiment, the total amount of CAP and the at least one processing aid range from about 14.9% to about 50% combined, e.g., from about 20% to about 50% and about 25% to about 40%, by weight of the total weight of the composition.

In one embodiment, the non-salified CAP is present in an amount ranging from about 10% to about 40% by weight, e.g., from about 10% to about 30% by weight, from about 15% to about 25% by weight, and from about 15% to about 20% by weight of the total weight of the aqueous composition.

In one embodiment, non-salified CAP is the only CAP present in the aqueous compositions or the described capsule shells or capsules of the present disclosure.

In one embodiment, processing aids are selected from poloxamers or mixtures thereof.

In one embodiment, the aqueous compositions described herein may comprise one or more (d) pharmaceutically acceptable agents, food acceptable colouring agents, or mixtures thereof.

Said agents may be selected from azo-, quinophthalone-, triphenylmethane-, xanthene- or indigoid dyes; iron oxides or hydroxides; titanium dioxide; or natural dyes and mixtures thereof. Further examples are patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, chlorophyllin, canthaxanthin, caramel, betanin and Candurin® pearlescent pigments. Candurin® is manufactured and marketed by Merck KGaA, Darmstadt, Germany and consist of titanium dioxide and/or iron oxide—approved food and pharmaceutical colorants in many countries—and potassium aluminium silicate as color carrier. The latter is a natural, also widely approved, silicate also known under the name of 'mica'.

In one embodiment, the pharmaceutically acceptable agents, food acceptable colouring agents, or mixtures thereof are present in an amount ranging from about 0 to about 5% by weight, e.g., from about 0 to about 2.5% by weight, and from about 0 to about 1.5% by weight over the total weight of the aqueous composition of the invention.

In one embodiment, the aqueous compositions described herein further comprise at least one film forming aid (e).

In one embodiment, the term "film forming aid" comprises one or more plasticizers conventionally used in the manufacture of capsule shells, notably hard capsule shells, and/or one or more viscosity enhancers, i.e. natural as well as synthetic substances conventionally used to optimize viscosity of aqueous compositions for the dip moulding manufacture of hard capsule shells. Film forming aids that display plasticizing properties include: phtalique esters (e.g. dimethyl-, diethyl-, dibutyl-, diisopropyl- and dioctyl-phtalate); citric esters (e.g. triethyl-, tributyl-, acetyltriethyl- and acetyltributyl-citrate); phosphoric esters (e.g. triethyl-, tricresyl, triphenyl-phosphate); alkyl lactate; glycerol and glycerol esters; oils and fatty acid esters; butyl stearate; dibutyl sebacate; dibutyl tartrate; diisobutyl adipate, tributyrin; propylene glycol; polyethyleneglycol (PEG), polyoxyethylene (PEO); and mixtures thereof.

In one embodiment, film forming aids are selected from thickening agents, structuring agents, surfactants, and plasticizers, e.g., hypromellose; alkyl cellulose and other cellulosic derivatives; polyvinyl acetate derivatives (PVAP); polysaccharides; glyceryl esters; glycol esters; sorbitan monoesters; sorbitan polyoxyethylene esters; polyoxyethylene (POE) ethers; glycerol; polyethylene glycols; polyols; fatty acid esters; glycerol polyethylene, glycol ricinoleate; macrogolglycerides; SLS; triethyl citrate (TEC); Triacetine; alkyl phtalate; and mixtures thereof.

In one embodiment, film forming aids are selected from HPMC, HPC, EC, MC, CMEC, HPMCAS, and HPMCP.

In one embodiment film forming aids that display compatibility with CAP are selected from cellulosic derivatives (e.g. HPMC, HPC) and mixtures thereof.

In one embodiment film forming aids that display viscosity enhancing properties are selected from: guar gum, xanthan, carrageenans, gellan gum, carboxymethyl cellulose (CMC), alkyl celluloses, polysaccharides, and mixtures thereof.

In one embodiment, film forming aids that display both plasticizing and viscosity enhancing properties are selected from: glyceryl esters (e.g. glyceryl monooleate and monolinoleate, medium chain triglycerides—i.e. $C_6$-$C_{12}$ fatty acid esters of glycerol); glycol esters (e.g. propylene glycol dicaprylocaprate and monolaurate); sorbitan monoesters (e.g. sorbitan monolaurate and monooleate); sorbitan polyoxyethylene esters (e.g. polyoxyethylene sorbitan monolaurate, monopalmitate, monostearate and monooleate); polyoxyethylene (POE) ethers (e.g. polyethylene glycol dodecyl ether); glycerol; polyethylene glycols (e.g. PEG 4000, PEG 6000); glycerol polyethylene glycol ricinoleate; linoleoyl macrogolglycerides; and mixtures thereof.

In one embodiment, film forming aids are selected from: sorbitan monoesters (e.g. sorbitan monolaurate and monooleate); sorbitan polyoxyethylene esters (e.g. polyoxyethylene sorbitan monolaurate, monopalmitate, monostearate and monooleate); polyoxyethylene (POE) ethers (e.g. polyethylene glycol dodecyl ether); glycerol; Polyvinyl acetate derivatives (PVAP), cellulosic derivative (e.g. HPMC, HPC, EC, MC, CMEC, HPMCAS, HPMCP) and mixtures thereof.

In one embodiment, film forming aids are present in the aqueous composition in an amount ranging from about 0 to about 15% by weight, such as about 0 to about 10% by weight, about 0 to about 8% by weight over the total weight of the aqueous composition of the invention.

In one embodiment, the water (c) is purified in a manner that is acceptable for pharmaceutical uses as defined under USP purified water in USP32 and USP34-NF29. It will be understood that the aqueous composition described herein allow for non-aqueous solvents in trace amounts. Typical non-aqueous solvents are for example ethanol, or other low MW alcohols conventionally used as solvents, chlorinated solvents, ethers.

In one embodiment, the aqueous compositions comprise ingredients a), b), c) and e) as defined above. In another embodiment, the aqueous compositions comprise ingredients a), b), c), d) and e) as defined above.

In one embodiment, the present disclosure also provides capsule shells comprising the aqueous compositions described herein, for example, as bulk enteric hard capsule shells.

In one embodiment, hard capsule shells are obtainable using the aqueous compositions disclosed above and the processes as disclosed below, e.g., dip moulding.

In one embodiment, the hard capsule shells as described comprise a shell thickness (after drying to bring the water content of the shell below 6% by weight over the weight of the shell) lower than about 250 µm, e.g., at about 150 µm, and at about 70 µm. Thus, in one embodiment, the shell thickness may range from about 70 to about 150 µm.

It should be noted that the aforementioned shell thickness values are difficult, if not impossible, to be obtain with manufacturing methods that are alternative to dip moulding. For example, injection moulding techniques typically produce shell thicknesses of about 300 to about 500 µm.

In one embodiment, the shells may or may not be externally coated with additional one or more polymer layers. Alternatively, the shells are monolayer, i.e., no external additional polymer layers are present. Thus, in one embodiment, no additional functional polymer layers are present.

Unless otherwise indicated, functional polymer layers means layers containing functional polymers that impart a particular mechanical or chemical properties to the coated shell. Functional polymers are enteric polymers conventionally used to coat pharmaceutical solid dosage forms and/or colonic release polymers (i.e. polymers used to achieve disintegration of the coated dosage form in the colon region of a subject). An overview of these polymers as applied to hard capsule coatings, can be found in, for example, WO 2000/018377. Capsule banding or sealing are not presently considered as applying additional external layer(s), hence banded or sealed capsule shells and capsule are well within the scope of the present disclosure.

In one embodiment, the present disclosure provides bulk enteric hard capsule shells comprising:

(A) non-salified cellulose acetate phthalate (CAP), said CAP being present in an amount ranging from about 40% to about 70% by weight of the total weight of said capsule shell;

(B) at least one processing aid present in an amount ranging from about 15% to about 49% by weight of the total weight of said capsule shell, wherein said at least one processing aid is selected from polyoxyethylene-polyoxypropylene-polyoxyethylene tri-block polymers or mixtures thereof, and comprise an average molecular weight ranging from about 1000 to about 20000 and a polyoxyethylene ratio ranging from about 10% to about 80%; and (C) water.

In one embodiment, the non-salified CAP is present in an amount ranging from about 45% to about 65% by weight or about 55% to about 65% by weight over the total weight of the shell.

In one embodiment, the processing aid is present in an amount ranging between about 20% to about 40% by weight or between about 30% to about 40% by weight over the total weight of said CAP in said composition and shell, respectively. The shell may comprise any one of the processing aids or mixtures of processing aids as discussed above in connection with the aqueous composition.

Typical amounts of water are below 20% by weight over the total weight of the shell, such as below 10% by weight, below 8% by weight, and below 6% by weight over the total weight of the shell.

In one embodiment, the amount of water, as equilibrated with the relative humidity of the outside air, ranges from about 2% to about 20% by weight of the total weight of the capsule shell.

In one embodiment, the hard capsule shells further comprise at least one encapsulated active ingredient. Thus, the capsules may be filled with one or more acid-instable substances and/or one or more substances associated with gastric side effects in humans and/or animals.

In one embodiment, acid-instable substances are natural or synthetic substances that undergo chemical degradation or modification in the acid environment present in the stomach of a subject. In one embodiment, substances associated with gastric side effects are pharmaceutical drugs or compositions intended for human or animal oral administration, whose release in the stomach upon oral administration to a human or animal being is associated to gastric side-effects, such as gastric reflux or impairment of physiological and/or structural integrity of gastric mucosa (e.g. stomach ulcers).

In one embodiment, the at least one active ingredient comprises a solid, semi-solid, or liquid form.

In one embodiment, the shells further comprise ingredient (D), one or more pharmaceutically or food acceptable colouring agents, as defined above. One or more pharmaceutically acceptable agents or food acceptable colouring agents are present in amounts ranging from 0 to about 15% by weight, such as, from 0 to about 10% by weight and from 0 to about 8% by weight over the total weight of the shells.

In one embodiment, the shells further comprise ingredient (E), film forming aids as defined above. Film forming aids may be present in amounts ranging from 0 to about 40% by weight, such as, from 0 to about 30% by weight and from 0 to about 25% by weight over the total weight of the shells.

In one embodiment, the shells may comprise ingredients A), B), C) and E) as defined above. In another embodiment, the shells may comprise ingredients A), B), C), D) and E) as defined above.

In one embodiment, the present disclosure also provides hard capsule shells and processes for making the hard capsule shells described herein, wherein the capsule shells comprise a disintegration release of less than about 10% of the total encapsulated at least one active ingredient after a time of about 2 hours and about pH 1.2.

In another embodiment, the present disclosure also provides hard capsule shells and processes for making the hard capsule shells described herein, wherein the capsule shells comprise a dissolution release of less than about 10% of the total encapsulated at least on active ingredient after at time of about 2 hours and about pH 1.2.

In one embodiment, the hard capsule shells comprise a disintegration release of less than about 10% of the total encapsulated at least one active ingredient after a time of about 2 hours and about pH 1.2 and a dissolution release of less than about 10% of the total encapsulated at least on active ingredient after at time of about 2 hours and about pH 1.2.

In one embodiment, the dissolution release is about 80% of the total encapsulated at least one active ingredient at a time of about 45 minutes and about pH 6.8.

In one embodiment, capsule shells have bulk enteric properties when they have dissolution and disintegration profiles that at least match the disintegration and dissolution profiles reported above. These disintegration and dissolution profiles in enteric media are difficult if not impossible to be achieved by capsule shells obtained using water based compositions containing lower amounts of enteric polymer (including CAP). Because conventional use has been to use the enteric polymer in solution and not the described dispersion, the use of much lower amounts of enteric polymer was a considered to be a mandatory feature, which does not apply here.

The described filled capsules may be made tamper-proof by using appropriate techniques to make the joint permanent. Typically, sealing or banding techniques can be used where these techniques are well-known to any skilled person in the field of capsules. In this connection, it is conventional practice to perform banding and/or sealing using polymer solutions in water/ethanol or water/isopropanol solutions. Traces of such non water solvents can be found if an elemental analysis is performed on a sealed or banded capsule without making a distinction between ingredients that are part of the shell and ingredients that are part of the band or sealing subsequently applied.

Processes to make the aforementioned capsule shells and capsules comprising the aqueous composition described herein are also disclosed. Despite the high solid content, the aqueous compositions described herein have low viscosity when the non-salified CAP is in a dispersed state and not in solution. The low viscosity of the aqueous solutions results in a dip moulding process that is easy and advantageous.

In one embodiment, the viscosity of the aqueous compositions described herein, when measured at 21° C. with a Brookfield viscosimeter equipped with a spindle 27 at a speed of 10 RPM, range from about 1 cP to about 5000 cP, e.g., from about 500 cP to about 3000 cP, and from about 1000 cP to about 2500 cP.

In one embodiment, the aqueous compositions to be used in the context of the dip-moulding processes described below are the aqueous compositions as discussed above. Accordingly, any consideration and embodiment discussed in connection with the aqueous compositions apply to the dip-moulding processes described herein to the extent that it is technically possible.

Accordingly, in one embodiment, the present disclosure provides dip-moulding processes for the manufacture of bulk enteric hard capsule shells, wherein the processes comprise:
  i) providing an aqueous composition comprising
    (a) an aqueous dispersion of non-salified cellulose acetate phthalate (CAP), said CAP being present in an amount ranging from about 10% to about 40% by weight of the total weight of said aqueous composition;
    (b) at least one processing aid present in an amount ranging from about 4% to about 20% by weight of the total weight of said aqueous composition,
    wherein said at least one processing aid is selected from polyoxyethylene-polyoxypropylene-polyoxyethylene triblock polymers or mixtures thereof, and comprise an average molecular weight ranging from about 1000 to about 20000 and a polyoxyethylene ratio ranging from about 10% to about 85%; and
    (c) water;
  ii) adjusting said aqueous composition to a temperature (T1) ranging from about 5° C. to about 40° C.;
  iii) pre-heating moulding pins at a dipping temperature (T2) ranging from about 15° C. to about 70° C. higher than said temperature T1;
  iv) dipping the pre-heated moulding pins into said aqueous composition;
  v) forming a film on said moulding pins by withdrawing said pins from said aqueous composition; and
  vi) drying the film on said moulding pins to form bulk enteric hard capsule shells.

In one embodiment, the aqueous composition is kept in step ii) at a temperature ranging from about 5° C. to about 40° C., such as, for example from about 15° C. to about 35° C. and about 15° C. to about 25° C.

In one embodiment, pins are pre-heated and dipped at a temperature ranging from about 15° C. to about 70° C. higher than the temperature of the aqueous composition in step ii). For example, the temperature may range from about 15° C. to about 50° C. and from about 25° C. to about 50° C. higher than the temperature of the aqueous composition in step ii). In one embodiment, pins are pre-heated to a temperature ranging from about 45° C. to about 90° C.

In one embodiment, step iv) comprises a single dipping of the pins. In other words, no multiple dipping of the pins is necessary to obtain a pick-up of material on pins surface sufficient to obtain a film endowed with required mechanical properties.

In one embodiment, step vi) of drying is performed according to drying techniques typically applied in the field of hard capsules, which can be accomplished using equipment known to the skilled person for this purpose. In one embodiment, step vi) of drying can be performed according to any technique commonly known for this purpose, for example by placing the pins in ovens. In one embodiment, step vi) of drying is performed at a temperature ranging from about 20° C. to about 90° C.

In one embodiment, the moulding processes further comprise a step vii) of filling hard capsules shells with one or more substances as disclosed above.

In one embodiment, the moulding processes further comprise a step viii) of making a filled hard capsule tamper-proof by sealing and/or banding the filled hard capsule obtained in step vii).

Without wanting to be bound by any theory, it is believed that the temperature T2 is high enough to induce coalescence in the aqueous composition. The temperature at which the aqueous composition coalesces can also be referred to as setting temperature, above the minimum film-forming temperature (MFFT). Setting temperature is a parameter of aqueous compositions to be used in the manufacture of hard capsules that is well known to any skilled person. The difference with conventional methods (e.g. thermogelling dip-moulding processes known for the manufacture of hard capsule shells using cellulose derivatives like HPMC) is that the setting temperature identifies the gelification of the composition whereas in the present disclosure it identifies the coalescence of the composition.

EXAMPLES

A suitable test procedure to test disintegration properties of the shells (and capsules) is as follows:

USP Apparatus basket-rack assembly consisting of six open-ended transparent tubes, each tube being provided with a disk; Disintegration media: simulated gastric fluid at pH 1.2 with NaCl for 2 h then simulated intestinal fluid at pH 6.8 with $KH_2PO_4$+NaOH; Test conditions: fluid kept at 37° C.; oscillation frequency was 30/min; volume of dissolution medium was 800 ml; number of samples tested was 6. Test shells #0 are pre-filled with 450 mg of a mix of lactose plus 0.1% B2 (indigo blue). Capsules are placed in the tubes and a disk is over imposed. The basket is then placed in the simulated gastric fluid for 2 h and then moved to the simulated intestinal fluid.

A suitable test procedure for dissolution properties of the shells (and capsules) is as follows:

USP Dissolution Apparatus 2 (paddle), dissolution media: simulated gastric fluid at pH 1.2 0.1N HCl for 2 h then simulated intestinal fluid at pH 6.8 with $Na_3PO_4$; Test conditions: fluid kept at 37° C., paddle vessel (USP/NF) of cylindrical form with spherical end; rotation speed was 50 rpm; dissolution liquid volume is 750 ml; number of samples is 6. Test shells #0 are filled with 380 mg of acetaminophen. Capsules are then placed into the vessel which is placed in the simulated gastric fluid for 2 h. Subsequently, 250 ml of 0.20M tribasic sodium phosphate are added to simulated intestinal fluid pH 6.8. UV ($\lambda$=300 nm) is used to quantify dissolved acetaminophen (as % of filled amount) in the dissolution media. Measures are made every 15 minutes when in the simulated gastric fluid and every 3 minutes in the simulated intestinal fluid.

When tested according to USP32-NF27 monographs <701> and <711> for delayed-release dosage forms, respectively, the capsule shells once filled with acetaminophen showed at least the following profiles:

Disintegration: release less than 10% of total encapsulated acetaminophen after 2 hours at pH 1.2; and Dissolution: release less than 10% of total encapsulated acetaminophen after 2 hours at pH 1.2, where 80% of the acetaminophen was released after 45 minutes at pH 6.8.

Description of the Test Protocols a) Determination of the Ability for the Aqueous Dispersion to Form a Continuous Film The prepared aqueous dispersion is casted on a hot (60° C.) glass plate using Capsugel film cast equipment (modified motorized Thin Layer Chromatography Plate Coater unit from CAMAG) or any other conventional drawdown coating equipment to make a uniform thin film having a dry thickness of about 100 µm. The casted film on the glass plate is kept in an oven during 1 hour at 60° C., and then stored for at least 2 hours at room temperature and 50% RH to allow full drying. Once dried, the obtained film is removed from the glass plate and evaluated for visual, physical properties, and thermal properties (including DSC and minimum film-forming temperature (MFFT) as per standard operating procedures for films and coating evaluation).

b) Evaluation of the Aqueous Dispersion Setting Properties

To reproduce the capsule dipping process, a simplified lab-scale equipment called Pin Lab Dipper has been developed to mimic the dipping of a pin into the solution. This device is equipped with an electronically-assisted module to control the pin dipping profile and withdrawal profile. It also ensures the pin rotation to the upright position and regulates the pin temperature. The dipping step is followed by a drying sequence with appropriate hot air. This test evaluates the potential setting properties of the tested solutions, whether it is possible to form a continuous and homogeneous film on the stainless steel pin by dip moulding processes.

Setting conditions for Example 1 below: dipping dish container at 21° C., pre-heated pin at 70° C., drying temperature 60° C. at room relative humidity. Visual control of capsule shell for possible defect, weight and thickness measurement (top wall, side wall and/or shoulder).

Example 1

Preparation of the Aqueous Dispersion

In a reactor of 300 mL, 60 g of Poloxamer (Lutrol L44 from BASF) are mixed with 140 mL of purified water under gentle stirring for 30 min. The obtained solution is poured in a 2-liter reactor containing 1000 g of Aquacoat CPD 30 dispersion from FMC at room temperature and stirred overnight for 12 hours for complete homogenization at 21° C. Usually, the viscosity of the formulation increases slightly from milk to liquid cream during this maturation step. A film and a capsule shell are prepared from this dispersion and evaluated according to the protocols described above under a) & b).

Example 2

Evaluation of Reduced Quantity of Poloxamer

In a reactor of 200 mL, 45 g of Poloxamer 124 (Lutrol L44) are mixed with 105 mL of purified water under gentle stirring for 30 min. The obtained solution is poured in a 2-liter reactor containing 1000 g of Aquacoat CPD 30 dispersion at room temperature and stirred overnight for 12 hours for complete homogenization at 21° C. (Example 2). A film and a capsule shell are prepared from this dispersion and evaluated according to the protocols described above under a) & b).

Example 3

In a reactor of 150 mL, 30 g of Poloxamer 124 (Lutrol L44) are mixed with 70 mL of purified water under gentle stirring for 30 min. The obtained solution is poured in a 2-liter reactor containing 1000 g of Aquacoat CPD 30 dispersion at room temperature and stirred overnight for 12 hours for complete homogenization at 21° C. (Example 3). A film and a capsule shell are prepared from this dispersion and evaluated according to the protocols described above under a) & b).

Results:

| Example # | Commercial name | poloxamer/ CAP ratio | film | viscosity (cP) (3) | Young modulus MPa (2) | Elongation at break % (2) | MFFT (° C.) | Tg (° C.) | capsule shell (1) |
|---|---|---|---|---|---|---|---|---|---|
| 1 | Lutrol L44 | 1/5 | uniform film | 1300 | 720 | 40 | 30 | 47 | adequate pick-up |
| 2 | Lutrol L44 | 3/20 | uniform film | 800 | 860 | 30 | 30 | 46 | satisfying pick-up |
| 3 | Lutrol L44 | 1/10 | cracked film | 21 | N/A | N/A | 30 | 45 | no pick up |

(1) pick up: formation of a continuous & homogeneous film of about 100 µm +/− 20 µm on the stainless steel pin
(2) film stored at 23% RH, measured with Instron 4443, 4 × 0.5 inches tensile specimens
(3) measured with Brookfield, spindle 27, 10 RPM, 21° C.

Examples 4-10

The aqueous dispersions of Examples 4, 5, 6, 7, 8, 9 and 10 have been prepared to compare various grades of poloxamer (Pluronic from BASF) according to the protocol described for Example 1, with respectively Pluronic F108, Pluronic F127, Pluronic F68, Pluronic F87, Pluronic L35, Pluronic L43, Pluronic L62 instead of Lutrol L44 in the same proportions: 1/5 (w/w) poloxamer (30% solution)/CAP (30% dispersion) ratio. A film and a capsule shell are prepared from this dispersion and evaluated according to the protocols described above under a) & b).

Results:

| Example # | Commercial name | Poloxamer grade (2) | Mw (2) | EO % (2) | HLB (2) | Observation |
|---|---|---|---|---|---|---|
| 4 | Pluronic F108 | 338 | 16500 | 80 | >24 | no pick up (1) |
| 5 | Pluronic F127 | 407 | 13333 | 70 | >24 | no pick up (1) |
| 6 | Pluronic F68 | 188 | 9000 | 80 | >24 | no pick up (1) |
| 7 | Pluronic F87 | 237 | 7666 | 70 | >24 | no pick up (1) |
| 8 | Pluronic L35 | N/A | 1900 | 50 | 18-23 | weak thin film formed |
| 1 | Lutrol L44 | 124 | 2000-2200 | 40 | 12-18 | adequate film formed |
| 9 | Pluronic L43 | N/A | 1850 | 30 | 7-12 | weak thick film formed |
| 10 | Pluronic L62 | 182 | 2450 | 20 | 1-7 | poor thick film formed |

(1) pick up: formation of a continuous & homogeneous layer/film on the stainless steel pin
(2) data according to BASF technical datasheets

Example 11

Evaluation of a Blend with Hypromellose (HPMC) as Film-Forming Aid

In a reactor of 300 mL, 60 g of Poloxamer 124 (Lutrol L44) are mixed with 140 ml of purified water under gentle stirring for 30 min. The obtained solution is poured in a 2-liter reactor containing 1000 g of Aquacoat CPD 30 dispersion and 600 g of a HPMC 20% solution at room temperature and stirred overnight for 12 hours for complete homogenization at 21° C. A film and a capsule shell are prepared from this dispersion and evaluated according to the protocols described above under a) & b).

Example 12

Evaluation of the Opacification

In a reactor of 300 mL, 60 g of Poloxamer 124 (Lutrol L44) are mixed with 140 mL of purified water under gentle stirring for 30 min. The obtained solution is poured in a 2-liter reactor containing 1000 g of Aquacoat CPD 30 dispersion at room temperature and stirred overnight for 12 hours for complete homogenization at 21° C. After maturation, a titanium dioxide slurry is added to the obtained dispersion under gentle stirring until complete homogenization at 21° C., at a ratio of 5/95 (w/w slurry/dispersion). The titanium dioxide slurry comprises 21.8% of $TiO_2$, 19.4% of a 20% HPMC solution, 58.1% of water pH 4 and 0.7% of a cationic compound such as chitosan. The chitosan is first pre-dispersed in the water pH 4 and the solution is defoamed overnight. $TiO_2$ is then added and dispersed 3×2 min at Vmax with a high speed homogenizer such as Ultra-Turrax. Then the HPMC solution is added and stirred 3 min at 1200 RPM with a high speed homogenizer. In addition, 0.2% of pigment Patented Blue dispersed in a minimum of water is optionally incorporated to the final preparation under gentle stirring to obtain an opaque blue film and capsule shell. A film and a capsule shell are prepared from this dispersion and evaluated according to the protocols described above under a) & b).

Example 13

Thickening agent: In a reactor of 200 mL, 45 g of Poloxamer 124 (Lutrol L44 from BASF) are mixed with 105 ml of purified water under gentle stirring for 30 min. In a separate beaker of 100 mL, 3 g of carboxymethyl cellulose (Blanose 7MF-PH from Ashland) are added to 72 mL of purified water under high speed homogenization, using for example an Ultra-Turrax homogenizer during 20 min before a 30 min-defoaming step under vacuum. Both obtained Poloxamer and Blanose solutions are poured in a 2-liter reactor containing 1000 g of Aquacoat CPD 30 dispersion at room temperature and stirred overnight for 12 hours for complete homogenization at 21° C. A film and a capsule shell are prepared from this dispersion and evaluated according to the protocols described above under a) & b).

Example 14

In a reactor of 300 mL, 60 g of polyoxyethylene (Polyox N10 from Dow) are mixed with 140 mL of purified water under gentle stirring (150 RPM) at 80° C. during one night. The obtained solution is then cooled down at room temperature and poured in a 2-liter reactor containing 1000 g of Aquacoat CPD 30 dispersion comprising 23% of non-salified CAP and about 7% of Poloxamer; the mixture is stirred during one night at 200 RPM for complete homogenization at 21° C. A film and a capsule shell are prepared from this dispersion and evaluated according to the protocols described above under a) & b).

Example 15

Gelling agent: In a reactor of 300 mL, 1.4 g of carrageenan (Satiagum UTC 10 grade lambda from Cargill) is mixed with 140 mL of purified water under gentle stirring for 30 min. Then 60 g of Poloxamer 124 (Lutrol L44) is added to this solution under gentle stirring for 30 min. The obtained solution is poured in a 2-liter reactor containing 1000 g of Aquacoat CPD 30 dispersion at room temperature and stirred overnight for 12 hours for complete homogenization at 21° C. A film and a capsule shell are prepared from this dispersion and evaluated according to the protocols described above under a) & b).

Results:

| Example # | film | viscosity (cP) (3) | Young modulus (MPa) (2) | Elongation at break % (2) | capsule shell (1) |
|---|---|---|---|---|---|
| 11 | uniform film | >2000 | 867 | 29 | adequate pick-up |
| 12 | uniform thick film | N/A | 515 | 45 | adequate opaque pick-up (optionnally blue) |
| 13 | uniform slightly bitty film | 1762 | 740 | 41 | satisfying pick-up |

-continued

| Example # | film | viscosity (cP) (3) | Young modulus (MPa) (2) | Elongation at break % (2) | capsule shell (1) |
|---|---|---|---|---|---|
| 14 | thick film | N/A | 669 | 12 | adequate pick-up |
| 15 | uniform transparent film | 1987 | 614 | 48 | adequate pick-up |

(1) pick up: formation of a continuous & homogeneous film on the stainless steel pin
(2) film stored at 23% RH, measured with Instron 4443, 4 x 0.5 inches tensile specimens
(3) measured with Brookfield, spindle 27, 10 RPM, 21° C.

Examples 16-18

Evaluation of various process conditions on PLD—Dispersion temperature: An aqueous dispersion of CAP and Poloxamer is prepared according to the Example 1. It is then poured into the dipping dish container of the electronically-assisted Pin Lab Dipper, in which a robotized hot pin at 70° C. is dipped and withdrawn according to a pre-established sequence before drying at 60° C. The dipping dish container temperature is respectively set at 14° C., 18° C. and 24° C. for Examples 16, 17 and 18.

Examples 19 and 20

Evaluation of various process conditions on PLD—Pin temperature: An aqueous dispersion of CAP and Poloxamer is prepared according to the example 1. It is then poured into the dipping dish container at 21° C. of the electronically-assisted Pin Lab Dipper, in which a robotized hot pin is dipped and withdrawn according to a pre-established sequence before drying at 60° C. The pin temperature is respectively set at 67° C. and 73° C. for the example 19 and 20.

Results:

| Example # | dish T ° C. | pin T ° C. | body * weight (g) | side wall * thickness (µm) | top wall * thickness (µm) | shoulder * thickness (µm) | viscosity (cP) (1) | Observation |
|---|---|---|---|---|---|---|---|---|
| 1 | 21 | 70 | 60 | 100 | 125 | 80 | 1350 | adequate pick-up |
| 16 | 14 | 70 | <40 | <60 | broken | broken | <800 | no pick up |
| 17 | 18 | 70 | 44 | 80 | 90 | 50 | 1150 | thin film |
| 18 | 24 | 70 | 68 | 120 | 150 | 85 | 1550 | thick film |
| 19 | 21 | 67 | 50 | 95 | 85 | 60 | 1350 | thin film |
| 20 | 21 | 73 | 60 | 110 | 125 | 80 | 1350 | slightly thick film |

* average data
(1) measured with Brookfield, spindle 27, 10 RPM, 21° C.

Example 21

Evaluation of the aqueous dispersions on pilot capsule machine: In a reactor of 1 L, 240 g of Poloxamer (Lutrol L44 from BASF) are mixed with 560 ml of purified water under gentle stirring for 30 min. The obtained solution is poured in a 5-liter reactor containing 4000 g of Aquacoat CPD 30 dispersion at room temperature and stirred overnight for 12 hours for complete homogenization at 21° C. Usually, the viscosity of the formulation increases slightly from milk to liquid cream during this maturation step.

Manufacture of the capsules with pilot machine: The defined aqueous dispersion is transferred into the dipping dish of a pilot machine of conventional hard capsule production equipment. While keeping the dipping solution at 21° C., hot stainless steel pins size 0 at 70° C. (pins body or cap are pre-heated at 70° C. in the corresponding section of the pilot machine) are dipped into the aqueous dispersion according to a well defined dipping profile in an attempt to manufacture capsules (body or cap) with the same dimension specifications to the conventional hard capsules. After withdrawal the dipped pins are transferred to a drying section where they are submitted to hot air at defined speed, temperature and humidity. When dry, the body or cap capsules parts obtained are stripped of the pins, cut and assembled for visual control and physical property measurements, including weight, dimensional evaluation, and dissolution/disintegration tests.

Examples 22 and 23

The aqueous dispersion is prepared according to the Example 21. It is then transferred into the dipping dish of a pilot machine of conventional hard capsule production equipment, to manufacture capsules following the same protocol as described for Example 21. The hot stainless steel pins are heated at 70° C. The dipping solution and the dipping dish container are kept at 19° C. and 23° C. for the respective Example 22 and 23.

Examples 24 and 25

The aqueous dispersion is prepared according to the Example 21. It is then transferred into the dipping dish of a pilot machine of conventional hard capsule production equipment, to manufacture capsules following the same protocol as described for example 21. The dipping solution and the dipping dish container are kept at 21° C. The hot stainless steel pins are respectively heated at 60° C. and 65° C. for the Examples 24 and 25.

Example 26

In a reactor of 1 L, 240 g of Poloxamer 124 (Lutrol L44) are mixed with 560 ml of purified water under gentle stirring for 30 min. The obtained solution is poured in a 5-liter reactor containing 4000 g of Aquacoat CPD 30 dispersion at room temperature and stirred overnight for 12 hours for complete homogenization at 21° C. After maturation, a titanium dioxide slurry is added to the obtained dispersion under gentle stirring until complete homogenization at 21° C., at a ratio of 5/95 (w/w slurry/dispersion). The titanium dioxide slurry comprises 21.8% of $TiO_2$, 19.4% of a 20% HPMC solution, 58.1% of water pH 4 and 0.7% of a cationic compound such as chitosan. The chitosan is first pre-dispersed in the water pH 4 and the solution is defoamed overnight. TiO$_2$ is then added and dispersed 3×2 min at Vmax with a high speed homogenizer such as Ultra-Turrax. Then the HPMC solution is added and stirred 3 min at 1200 RPM with a high speed homogenizer.

In addition, 0.25% of pigment yellow 6 dispersed in a minimum of water is optionally incorporated to the final preparation under gentle stirring at 21° C. to obtain an opaque orange capsule shell.

The defined aqueous dispersion is transferred into the dipping dish of a pilot machine of conventional hard capsule production equipment. While keeping the dipping solution at 21° C., hot stainless steel pins size 0 at 70° C. (pins body or cap are pre-heated at 70° C. in the corresponding section of the pilot machine) are dipped into the aqueous dispersion according to a well defined dipping profile in an attempt to manufacture capsules (body or cap) with the same dimension specifications to the conventional hard capsules. After withdrawal the dipped pins are transferred to a drying section where they are submitted to hot air at defined speed, temperature and humidity. When dry, the body or cap capsules parts obtained are stripped of the pins, cut and assembled for visual control and physical property measurements, including weight, dimensional evaluation, and dissolution/disintegration tests.

Results:

| Example # | dish T ° C. | pin T ° C. | body * weight (g) | side wall * thickness (µm) | top wall * thickness (µm) | shoulder * thickness (µm) | viscosity (cP) | Observation defects |
|---|---|---|---|---|---|---|---|---|
| 21 | 21 | 70 | 62 | 107 | 124 | 88-144 | 127 (1) | adequate capsule |
| 22 | 19 | 70 | 56 | N/A | 183 | N/A | 137 (1) | many visual defects |
| 23 | 23 | 70 | 67 | N/A | 198 | N/A | 194 (1) | many visual defects |
| 24 | 21 | 60 | 53 | N/A | 95 | N/A | 213 (2) | thin capsule |
| 25 | 21 | 65 | 58 | N/A | 152 | N/A | 182 (2) | adequate capsule |
| 26 | 21 | 70 | 63 | 110 | 190 | 89 | 180 (1) | adequate white capsule (optionally orange) |
| 27 | 21 | 70 | 60 | 109 | 117 | 85 | 530 (1) | adequate harder capsule |

* average data for selected defined dipping profile
Viscosity measured with Capsugel pilot machine viscosimeter;
speed (1) v = 3
(2) v = 5

Dissolution profile of a capsule shell containing acetaminophen. UV-titration (300 nm)

| | time (min) | 0 | 15 | 30 | 45 | 60 | 75 | 90 | 105 | 120 | 123 |
|---|---|---|---|---|---|---|---|---|---|---|---|
| Example 21 | % dissolved | 0.00 | 0.10 | 0.30 | 0.55 | 0.80 | 1.02 | 1.25 | 1.45 | 1.62 | 2.88 |
| Example 26 | % dissolved | 0.00 | 0.07 | 0.35 | 0.66 | 0.98 | 1.32 | 1.62 | 1.90 | 2.16 | 3.79 |

| | time (min) | 126 | 129 | 132 | 135 | 140 | 145 | 150 | 155 | 170 | 185 |
|---|---|---|---|---|---|---|---|---|---|---|---|
| Example 21 | % dissolved | 8.44 | 20.23 | 34.58 | 47.75 | 65.30 | 77.54 | 85.55 | 97.74 | 99.36 | 100.00 |
| Example 26 | % dissolved | 6.10 | 14.97 | 32.97 | 50.90 | 71.71 | 84.28 | 91.17 | 99.04 | 98.98 | 99.11 |

Example 27

In a reactor of 1 L, 240 g of Poloxamer 124 (Lutrol L44) are mixed with 560 mL of purified water under gentle stirring for 30 min. The obtained solution is poured in a 5-liter reactor containing 4000 g of Aquacoat CPD 30 dispersion and 2400 g of a HPMC 20% solution at room temperature and stirred overnight for 12 hours for complete homogenization at 21° C.

The defined aqueous dispersion is transferred into the dipping dish of a pilot machine of conventional hard capsule production equipment. While keeping the dipping solution at 21° C., hot stainless steel pins size 0 at 70° C. (pins body or cap are pre-heated at 70° C. in the corresponding section of the pilot machine) are dipped into the aqueous dispersion according to a well defined dipping profile in an attempt to manufacture capsules (body or cap) with the same dimension specifications to the conventional hard capsules. After withdrawal the dipped pins are transferred to a drying section where they are submitted to hot air at defined speed, temperature and humidity. When dry, the body or cap capsules parts obtained are stripped of the pins, cut and assembled for visual control and physical property measurements, including weight, dimensional evaluation, and dissolution/disintegration tests.

As discussed above, existing process to obtain enteric (not necessarily bulk enteric) capsules, e.g., double dipping techniques or post-manufacturing techniques, require the use of multiple steps, which is contrary to the present disclosure. Without wanting to be bound by any theory, it is believed that the dip-moulding processes described herein entail coalescence of the aqueous composition on the surface of a conventional pin, assisted by a thermo-gelling phenomenon due to the use of the processing aid b) that is able to form thermo-reversible gels at elevated temperature. In coalescence, it is considered that evaporation of water occurs while boundaries between CAP dispersed particles disappear, then the particles close-pack and lead to an uniform phase domain; as per continuing evaporation and particle compaction, polymer film starts forming with compacted (deformed) CAP particles, leading to inter-particles diffusion of CAP polymer molecules that generate isotropic polymer film. Thus, the present disclosure provides coalescing dip-moulding techniques on the aqueous CAP dispersion described above, wherein hard capsule shells can be obtained that display bulk enteric properties without the need to repeatedly (e.g. double) dip the pins or apply further external enteric coatings to the already manufactured shells. By juxtaposition to the presently disclosed "one step" processes, earlier processes require at least a "second" step which may be the second pin dipping step or the application step of a capsule coating.

Furthermore, the present disclosure also accomplishes, in part, 1) the use of aqueous compositions comprising an aqueous dispersion of non-salified CAP; 2) the use of aqueous compositions as opposed to non-aqueous (or solvent-based) CAP solutions, together with processing aid (b); 3) the production of films on the moulding pins surface by inducing coalescence of CAP dispersed particles in contrast to polymer gelification; 4) the production of films on the moulding pins surface without the need for other conventional based film-forming polymer(s); 5) the ability to use of higher amounts of CAP polymer; and 6) increased viscosity of the aqueous compositions described herein that is otherwise unattainable by different processes outside the scope of the present disclosure.

What is claimed is:

1. An aqueous composition for the manufacture of enteric hard capsule shells, comprising:
    (a) an aqueous dispersion of non-salified cellulose acetate phthalate (CAP), said CAP being present in an amount ranging from about 10% to about 40% by weight of the total weight of said aqueous composition;
    (b) at least one processing aid present in an amount ranging from about 4% to about 20% by weight of the total weight of said aqueous composition, wherein said at least one processing aid is selected from polyoxyethylene-polyoxypropylene-polyoxyethylene tri-block polymers or mixtures thereof, having an average molecular weight ranging from about 1000 to about 20000 and a polyoxyethylene ratio ranging from about 10% to about 85%; and
    (c) water.

2. The composition according to claim 1, wherein the total amount of the CAP and the at least one processing aid range from about 14.9% to about 50% combined, by weight of the total weight of the composition.

3. The composition according to claim 1, wherein the CAP is in the form of finely divided solid particles having an average diameter ranging from about 0.1 to about 10 microns.

4. The composition according to claim 1, wherein the at least one processing aid is selected from poloxamers or mixtures thereof.

5. The composition according to claim 1, further comprising at least one pharmaceutically acceptable or food acceptable colouring agent.

6. The composition according to claim 1, further comprising at least one film forming aid.

7. The composition according to claim 6, wherein the at least one film forming aid is selected from thickening agents, structuring agents, surfactants, and plasticizers.

8. The composition according to claim 6, wherein the at least one film forming aid is selected from hypromellose; alkyl cellulose and other cellulosic derivatives; polyvinyl acetate derivatives (PVAP); polysaccharides; glyceryl esters; glycol esters; sorbitan monoesters; sorbitan polyoxyethylene esters; polyoxyethylene (POE) ethers; glycerol; polyethylene glycols; polyols; fatty acid esters; glycerol polyethylene, glycol ricinoleate; macrogolglycerides; SLS; triethyl citrate (TEC); Triacetine; alkyl phthalate; and mixtures thereof.

9. The composition according to claim 7, wherein the at least one film forming aid is selected from HPMC, HPC, EC, MC, CMEC, HPMCAS, and HPMCP.

10. A dip-moulding process for the manufacture of bulk enteric hard capsule shells, comprising:
    i) providing an aqueous composition comprising
        (a) an aqueous dispersion of a non-salified cellulose acetate phthalate (CAP), said CAP being present in an amount ranging from about 10% to about 40% by weight of the total weight of said aqueous composition;
        (b) at least one processing aid present in an amount ranging from about 4% to about 20% by weight of the total weight of said aqueous composition, wherein said at least one processing aid is a polyoxyethylene-polyoxypropylene-polyoxyethylene tri-block polymer or a mixture of polyoxyethylene-polyoxypropylene-polyoxyethylene tri-block polymers, and having an average molecular weight ranging from about 1000 to about 20000 and a polyoxyethylene ratio ranging from about 10% to about 85%; and
        (c) water;
    ii) adjusting said aqueous composition to a temperature (TI) ranging from about 5° C. to about 40° C.;
    iii) pre-heating moulding pins to a dipping temperature (T2) ranging from about 15° C. to about 70° C. higher than said temperature T1;
    iv) dipping the pre-heated moulding pins into said aqueous composition;
    v) forming a film on said moulding pins by withdrawing said pins from said aqueous composition; and
    vi) drying the film on said moulding pins to form bulk enteric hard capsule shells.

11. The process according to claim 10, wherein T1 ranges from about 15° C. to about 35° C.

12. The process according to claim 10, wherein T2 ranges from about 25° C. to about 50° C. higher than said temperature TI.

13. The process according to claim 10, wherein step iv) comprises a single dipping of the pins.

14. The process according to claim 10, further comprising a step vii) filling said hard capsule shells with at least one active ingredient.

15. A bulk enteric hard capsule shell comprising:
    (A) non-salified cellulose acetate phthalate (CAP), said CAP being present in an amount ranging from about 40% to about 70% by weight of the total weight of said capsule shell;
    (B) at least one processing aid present in an amount ranging from about 15% to about 49% by weight of the total weight of said capsule shell, wherein said at least one processing aid is selected from polyoxyethylene-polyoxypropylene-polyoxyethylene tri-block polymers or mixtures thereof, and having an average molecular weight ranging from about 1000 to about 20000 and a polyoxyethylene ratio ranging from about 10% to about 80%; and
    (C) water, wherein the capsule shell is produced by the process of claim 10.

16. The hard capsule shell according to claim 15, further comprising at least one encapsulated active ingredient.

17. The hard capsule shell according to claim 16, wherein the amount of water, as equilibrated with the relative humidity of the outside air, ranges from about 2% to about 20% by weight of the total weight of the capsule shell.

18. The hard capsule shell according to claim 17, wherein the at least one active ingredient comprises a solid, semi-solid, or liquid form.

19. The hard capsule shell according to claim 15, comprising
    a disintegration release of less than about 10% of the total encapsulated at least one active ingredient after a time of about 2 hours at a pH of about 1.2; and
    a dissolution release of less than about 10% of the total encapsulated at least one active ingredient after at time of about 2 hours at a pH of about 1.2.

20. The hard capsule shell according to claim 19, wherein the dissolution release is about 80% of the total encapsulated at least one active ingredient at a time of about 45 minutes at a pH of about 6.8.

\* \* \* \* \*